US011395929B2

(12) United States Patent
Kuusela et al.

(10) Patent No.: US 11,395,929 B2
(45) Date of Patent: Jul. 26, 2022

(54) METHOD AND APPARATUS TO DELIVER THERAPEUTIC RADIATION TO A PATIENT

(71) Applicant: Varian Medical Systems International AG, Steinhausen (CH)

(72) Inventors: Esa Kuusela, Espoo (FI); Mikko Hakala, Helsinki (FI); Shahab Basiri, Helsinki (FI); Elena Czeizler, Helsinki (FI)

(73) Assignee: Varian Medical Systems International AG, Steinhausen (CH)

( * ) Notice: Subject to any disclaimer, the term of this patent is extended or adjusted under 35 U.S.C. 154(b) by 0 days.

(21) Appl. No.: 17/031,063

(22) Filed: Sep. 24, 2020

(65) Prior Publication Data

US 2022/0088418 A1   Mar. 24, 2022

(51) Int. Cl.
*A61N 5/10* (2006.01)
(52) U.S. Cl.
CPC ........... *A61N 5/1081* (2013.01); *A61N 5/103* (2013.01); *A61N 2005/1092* (2013.01)
(58) Field of Classification Search
None
See application file for complete search history.

(56) References Cited

U.S. PATENT DOCUMENTS

2006/0262898 A1  11/2006  Partain et al.
2014/0270077 A1*  9/2014  Etmektzoglou ........ A61N 5/107
                                                        378/65

FOREIGN PATENT DOCUMENTS

EP    277776668 A1    9/2014
WO     9200656 A1     1/1992
WO     9200657 A1     1/1992

OTHER PUBLICATIONS

International Search Report and Written Opinion from related International Application No. PCT/EP2021/075521 dated Jan. 11, 2022; 16 pages.

* cited by examiner

*Primary Examiner* — Hoon K Song
(74) *Attorney, Agent, or Firm* — Fitch, Even, Tabin & Flannery LLP

(57) ABSTRACT

These teachings serve to facilitate radiating a treatment target in a patient during a radiation treatment session with a radiation treatment platform having a moving source of radiation and using an optimized radiation treatment plan. These teachings in particular provide for configuring the radiation treatment platform in a half-fan trajectory arrangement. These teachings then provide for beginning the radiation treatment session with the source of radiation in a first location and an isocenter for the treatment target in a first position. Then, during the radiation treatment session, these teachings provide for moving the source of radiation from that first location in synchronization with moving the isocenter from the aforementioned first position.

20 Claims, 4 Drawing Sheets

METHOD AND APPARATUS TO DELIVER THERAPEUTIC RADIATION TO A PATIENT

TECHNICAL FIELD

These teachings relate generally to treating a patient's planning target volume with radiation pursuant to a radiation treatment plan.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted material and adjacent tissues, organs, or the like that are desired or even critical to continued survival of the patient. As a result, radiation is ordinarily applied in a carefully administered manner to at least attempt to restrict the radiation to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

Many radiation treatment platforms include one or more multi-leaf collimators. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and which can selectively move towards and away from one another. A typical multi-leaf collimator has many such pairs of leaves, often upwards of twenty, fifty, or even one hundred such pairs.

While an effective accoutrement in many cases, multi-leaf collimators sometimes give rise to corresponding problems. Multi-leaf collimators typically provide either thick leaves (i.e., 0.5 to 1.0 cm in thickness) or offer only a limited field size. Small treatment targets, however, are typically too small for thick leaves to support a high-quality treatment plan while larger targets can be too large to be covered by the maximum-sized aperture available with the multi-leaf collimator.

BRIEF DESCRIPTION OF THE DRAWINGS

The above needs are at least partially met through provision of the method and apparatus to facilitate generating a deliverable therapeutic radiation treatment plan described in the following detailed description, particularly when studied in conjunction with the drawings, wherein.

Figure 1:
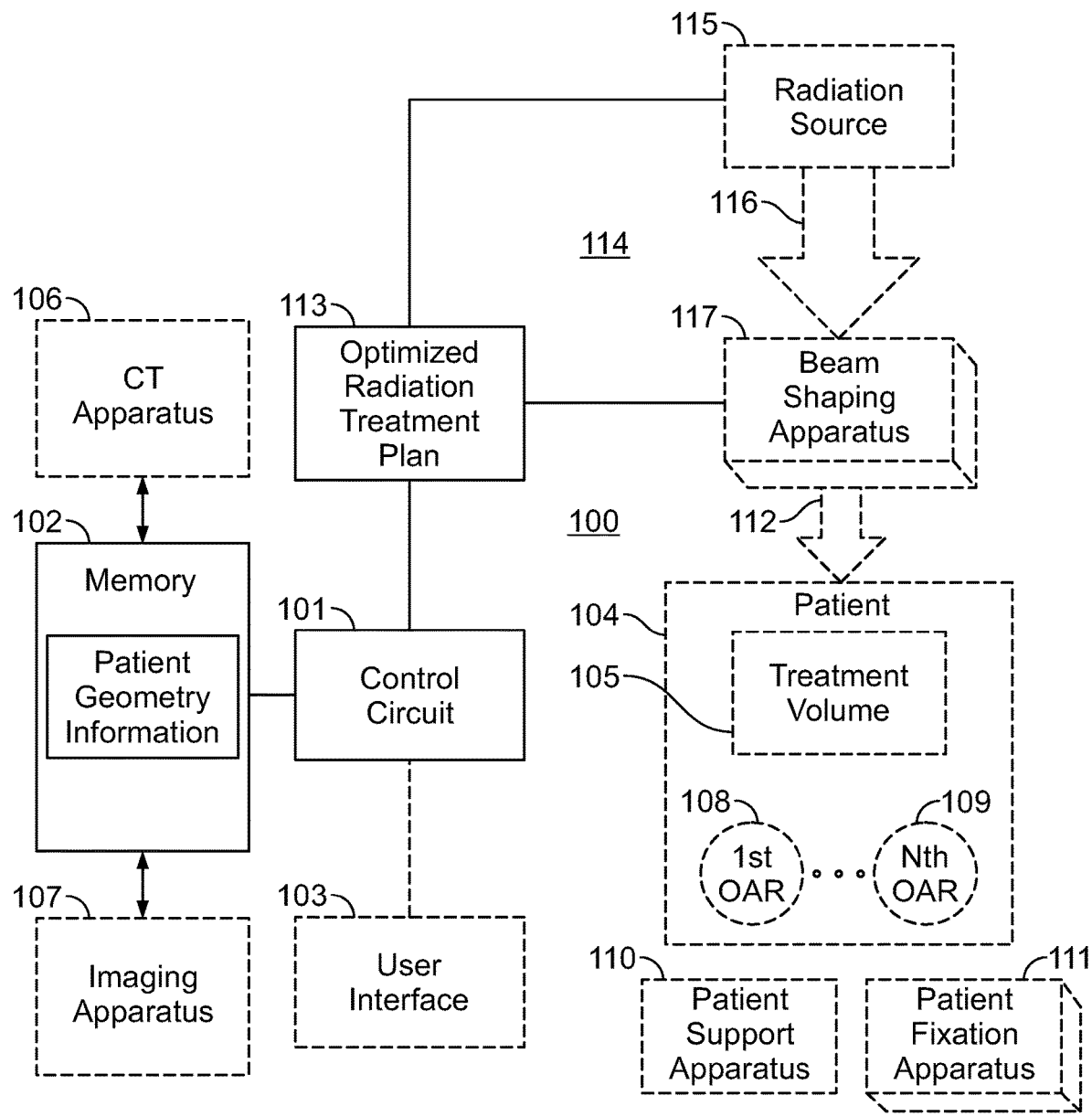
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate radiating a treatment target in a patient during a radiation treatment session with a radiation treatment platform having a moving source of radiation and using an optimized radiation treatment plan. These teachings provide for configuring the radiation treatment platform in a half-fan trajectory arrangement. These teachings then provide for beginning the radiation treatment session with the source of radiation in a first location and an isocenter for the treatment target in a first position. Then, during the radiation treatment session, these teachings provide for moving the source of radiation from that first location in synchronization with moving the isocenter from the aforementioned first position.

By one approach these teachings provide for moving the isocenter by moving a patient-supporting couch that comprises a part of the radiation treatment platform. If desired, the source of radiation is moved via a gantry that comprises a part of the radiation treatment platform. By one approach the source of radiation moves along an arcuate gantry pathway that may comprise, for example, a circular arc exceeding 180° in curvature about the patient. These teachings are highly flexible in these regards and will accommodate, for example, the arcuate pathway comprising an arc of at least 350° in curvature about the patient.

By one approach these teachings will further accommodate specifying the aforementioned half-fan trajectory arrangement for the radiation treatment platform and then optimizing a radiation treatment plan for radiation treatment platform parameters other than the half-fan trajectory arrangement to thereby provide the aforementioned optimized radiation treatment plan. So configured, optimization of the radiation treatment plan may comprise not optimizing the pre-determined half-fan trajectory pattern. By one approach, specifying that half-fan trajectory arrangement comprises specifying a pre-determined trajectory pattern.

These teachings are flexible in practice and will accommodate various modifications and/or supplemental activity. As one example in these regards, moving the source of radiation from the first location in synchronization with moving the isocenter from the first position can comprise simultaneously moving, for at least part of the radiation treatment session, both the source of radiation and the isocenter.

So configured, treatment targets that are otherwise too large to completely irradiate using a single field due, for example, to aperture size limitations for a utilized multi-leaf collimator can nevertheless be fully treated during the overall course of treatment. By one approach, the foregoing benefit is attained without increasing the complexity of the radiation treatment plan optimization process by excluding trajectory path parameters from automatic variation and testing during the optimization process.

These and other benefits may become clearer upon making a thorough review and study of the following detailed description. Referring now to the drawings, and in particular to FIG. 1, an illustrative apparatus 100 that is compatible with many of these teachings will be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to optimization objectives information, patient geometry information, field geometry information, half-fan trajectory parameters, and so forth, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized radiation treatment plan 113. This radiation treatment plan 113 typically comprises specified values for each of a variety of treatment-platform parameters during each of a plurality of sequential fields. In this case the radiation treatment plan 113 is generated through an optimization process. Various automated optimization processes specifically configured to generate such a radiation treatment plan are known in the art. As the present teachings are not overly sensitive to any particular selections in these regards, further elaboration in these regards is not provided here except where particularly relevant to the details of this description.

By one approach the control circuit 101 can operably couple to a radiation treatment platform 114 that is configured to deliver therapeutic radiation 112 to a corresponding patient 104 in accordance with the optimized radiation treatment plan 113. These teachings are generally applicable for use with any of a wide variety of radiation treatment platforms. In a typical application setting the radiation treatment platform 114 will include a radiation source 115 that can be selectively moved via a gantry along an arcuate pathway. The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

The radiation source 115 can comprise, for example, a radio-frequency (RF) linear particle accelerator-based (linac-based) x-ray source, such as the Varian Linatron M9. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical radiation treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more beam-shaping apparatuses 117 (such as jaws, multi-leaf collimators, and so forth) to provide selective beam shaping and/or beam modulation as desired. In a typical application setting, it is presumed herein that the patient support apparatus 110 is selectively controllable to move in any direction (i.e., any X, Y, or Z direction) during a radiation treatment session by the control circuit 101. As the foregoing elements and systems are well understood in the art, further elaboration in these regards is not provided here except where otherwise relevant to the description.

Figure 2:
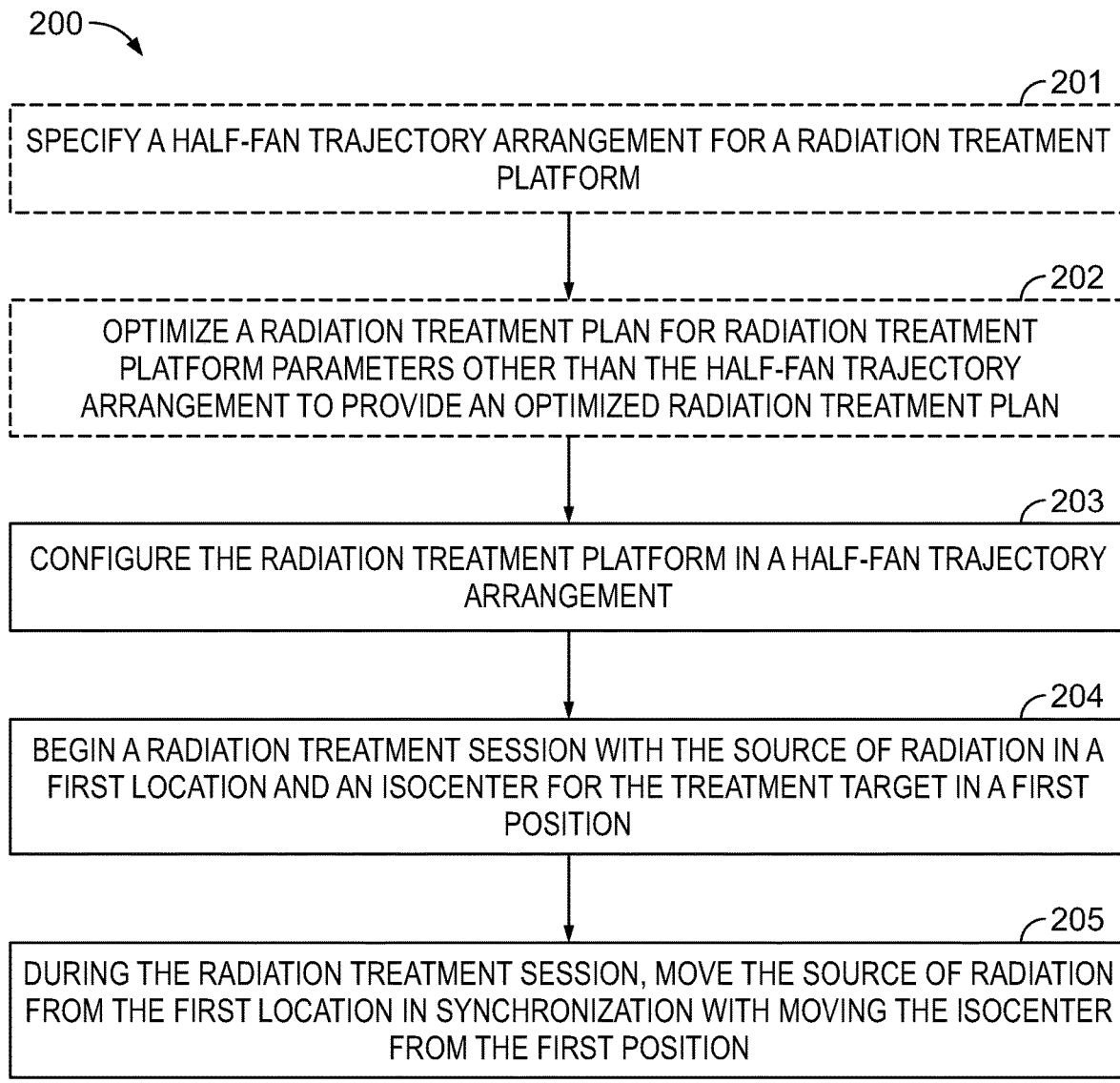
FIG. 2 comprises a flow diagram as configured in accordance with various embodiments of these teachings.

Referring now to FIG. 2, a process 200 that can be carried out, for example, in conjunction with the above-described application setting will be described. Generally speaking, this process 200 serves to radiate a treatment target (105) in a patient (104) during a radiation treatment session with a radiation treatment platform (114) having a moving source of radiation (115) using an optimized radiation treatment plan (113).

At optional block 201, this process 200 can provide for specifying a half-fan trajectory arrangement for the radiation treatment platform 114. By one approach this comprises specifying a pre-determined trajectory pattern.

Half-fan trajectory arrangements are known and understood in the art, though more typically in an imaging context during, for example, cone beam computed tomography (CBCT). In the latter regards, a small image planner is used that is of insufficient size to capture enough data for a large CBCT volume using a so-called half-fan approach where the panel is located asymmetrically around the KV-source centerline. In a typical arrangement the 2-D image is captured for only half of the targeted region, but once the gantry moves full-circle, all directions are covered and a complete image of the targeted region obtained.

Those skilled in the art understand that the expression "half-fan" is a useful naming convention that is not intended to be literally accurate. That is, any given exposure field is not necessarily exactly one half of the targeted region. Instead, it is understood that most fields, and many times every field, only expose part of the complete targeted region.

At optional block 202, this process 200 can then provide for optimizing a radiation treatment plan for radiation treatment platform parameters other than the half-fan trajectory arrangement to thereby provide the optimized radiation treatment plan 113. So configured, the parameters that specify and control the aforementioned half-fan trajectory arrangement (for example, parameters corresponding to a pre-determined radiation source trajectory pattern) are static and will not be varied during the optimization process to test variations regarding that half-fan trajectory arrangement. Other examples in these regards include, but are not limited to, jaw configurations, collimator angles, multi-leaf collimator carriage locations, beam energy, and, at least in an appropriate application setting, the maximum utilized dose rate. These teachings would also accommodate pre-defining certain sectors (between, for example, the starting and ending angles of the corresponding arc) where no radiation is delivered.

At block 203, this process 200 provides for configuring the radiation treatment platform 114 in a half-fan trajectory arrangement. This can comprise, for example, configuring the radiation treatment platform 114 per the half-fan trajectory arrangement specified at block 201 described above.

At block 204, this process 200 then begins the radiation treatment session with the source of radiation 115 in a first location and an isocenter for the treatment target 105 in a first position. Those skilled in the art understand that the isocenter is the point in space through which the central beam of radiation 112 passes. More precisely, the isocenter is a point in space relative to the treatment machine about which various components of the system rotate. In a typical application setting, gantry-based rotation of the radiation source 115 defines a first axis that cuts a second axis defined by rotation around the patient support apparatus 110. In a typical application setting the beam shaping apparatuses 117 will also rotate about an axis that points through the isocenter. These teachings will also accommodate employment with a robotic patient support system where the robot arm does not have a set rotation axis going through the isocenter, but where the robot is able (by coordinated motion of its joints) to move the patient to achieve an effective rotation around an axis passing through the isocenter. Yet another way to define the isocenter for many current machines would be to leverage the common point in beam centerlines from various gantry angles.

In a typical prior art application setting, the source of radiation will begin in a first location and then move along an arcuate path around the patient 104. More particularly, the isocenter, typically located within the treatment volume 105, will not move during the treatment session. Pursuant to the current process 200, however, during the radiation treatment session 115 the radiation source will move from the aforementioned first location in synchronization with movement of the isocenter from the aforementioned first position. While movement of the source of radiation 115 will typically comprise moving the latter via a gantry that comprises a part of the radiation treatment platform 114, moving the isocenter can be accomplished by moving the patient support apparatus 110 (for example, by moving a patient-supporting couch that comprises a part of the radiation treatment platform).

In support of the half-fan trajectory arrangement, movement of the source of radiation 115 may comprise moving the source of radiation 115 along an arcuate pathway that exceeds, for example, 180° in curvature about the patient up to and including an arc of at least 350° in curvature about the patient.

The aforementioned synchronized movement of the isocenter in conjunction with movement of the source of radiation 115 may comprise, for at least part of the radiation treatment session and possibly the entire radiation treatment session, simultaneous movement of both the source of radiation 115 and the isocenter. The teachings will also accommodate synchronized movement between these two factors that does not include simultaneous movement of both the source of radiation 115 and the isocenter.

So configured, these teachings permit the modulation of fluence within a relatively larger treatment volume 105 notwithstanding a limited space angle that characterizes the radiation treatment platform 114. Although only a part of the treatment volume 105 is irradiated from most or all angles, beams from opposing treatment directions serve, in the aggregate, to satisfactorily treat the entire treatment volume 105. These teachings will support, for example, treating treatment volumes that are especially wide in an X/Y direction by leveraging directional couch movement to thereby facilitate satisfactory dosing with a multi-leaf collimator that can otherwise only modulate a limited radiation cone in comparison to the dimensions of the treatment volume 105.

Those skilled in the art will appreciate that these teachings do not require elaborate trajectory optimization. Instead, the latter can be defined, for example, by simply using geometrical tools. It will also be appreciated that these teachings can be configured to seam the dose delivered from opposing directions to reduce the effect of intra-fraction patient motion.

Some specific examples in the foregoing regards will now be presented. It shall be understood that the specific details of these examples are intended to serve an illustrative purpose and are not intended to suggest any particular limitations with respect to these teachings.

Figure 3:
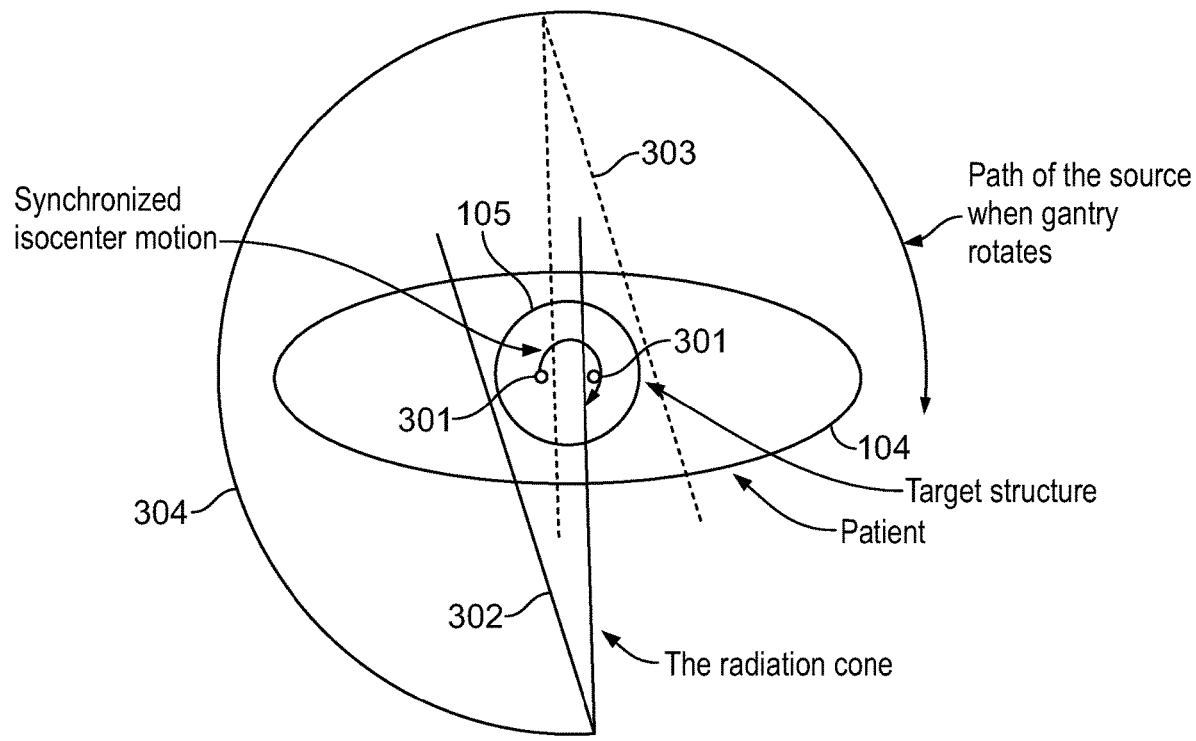
FIG. 3 comprises a schematic view as configured in accordance with various embodiments of these teachings.

FIG. 3 schematically depicts the use of half-fan arcs corresponding to radiation cones where two illustrative opposing radiation cones that combine to fully irradiate the target structure that constitutes the treatment volume 105 for this patient 104 are denoted by reference numerals 302 and 303. This figure also illustrates synchronized movement of the isocenter 301, which movement, in combination with movement of the radiation source 115 around the gantry path 304, permits the radiation cone that is otherwise too small to cover the entire treatment volume 105 to in fact nevertheless fully cover that structure. As described above, that movement of the isocenter 301 occurs by way of controlled and selective movement of the patient 104 via corresponding controlled and selective movement of the patient support apparatus 110 via, for example, the control circuit 101. It will be appreciated that the selective movement may be in any useful direction, and specifically in any direction in the X, Y, or Z directions (presuming a Cartesian point of reference).

Figure 4:
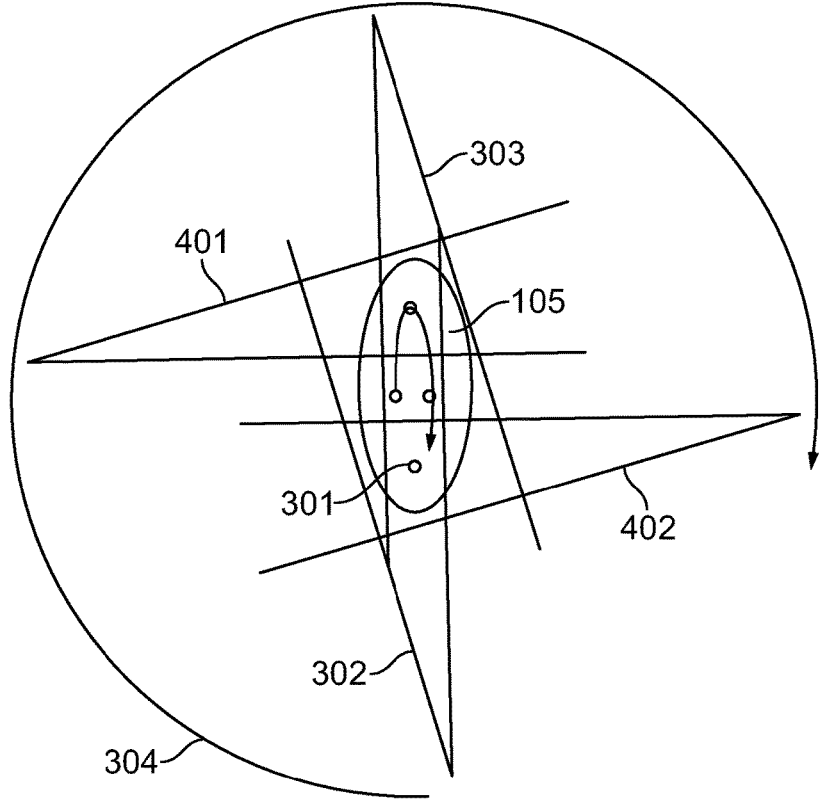
FIG. 4 comprises a schematic view as configured in accordance with various embodiments of these teachings.

FIG. 4 schematically depicts the use of half-fan arcs corresponding to radiation cones where a first pair of illustrative opposing radiation cones that combine to fully irradiate the target structure that constitutes the treatment volume 105 for this patient 104 are denoted by reference numerals 302 and 303 and a second pair of illustrative opposing radiation cones are denoted by reference numerals 401 and 402. In this example the treatment volume 105 has an elongated shape. In this case the synchronized movement of the isocenter 301 follows an oval-shaped path in order to best accommodate the shape of the treatment volume 105.

Figure 5:
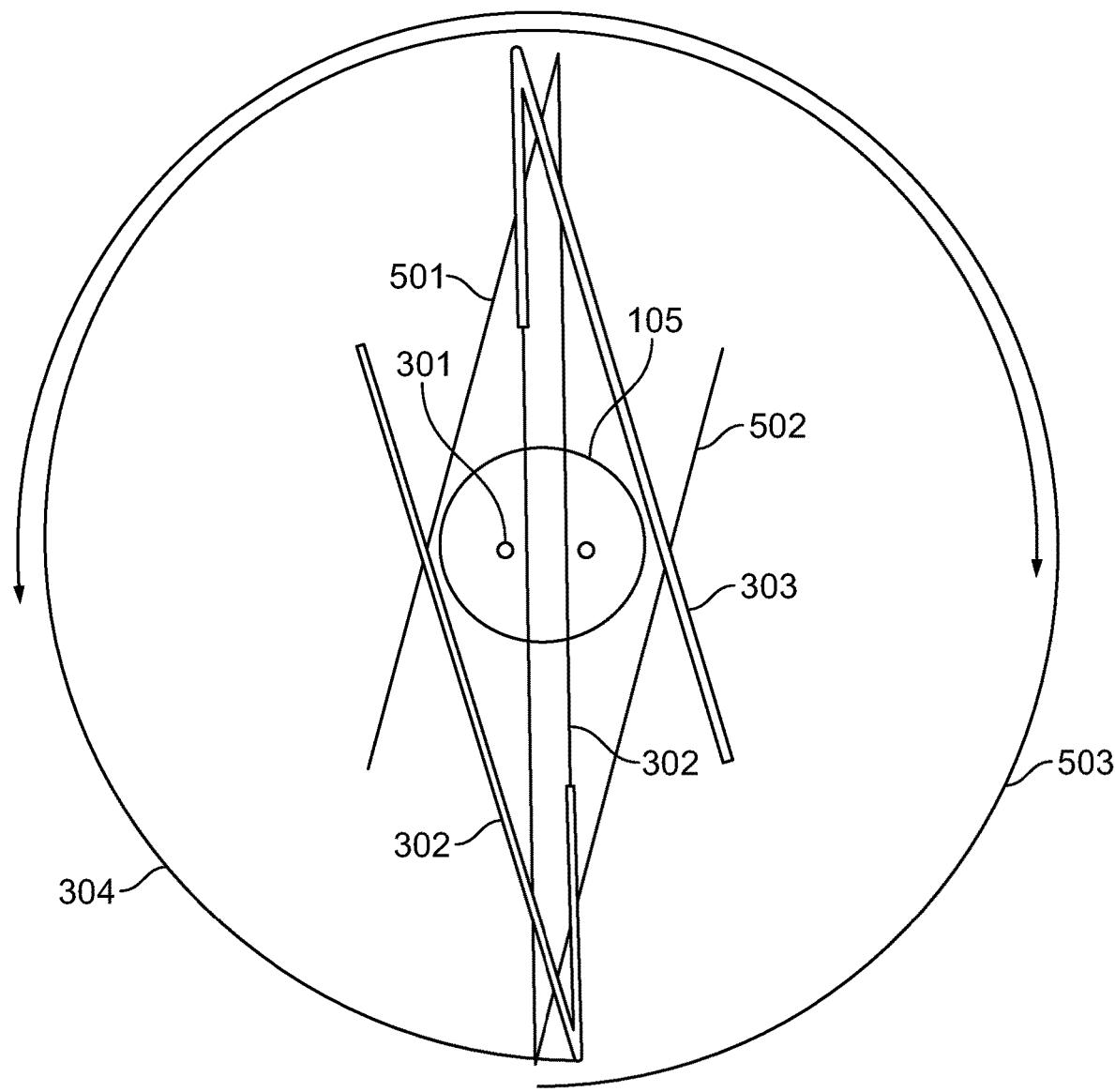
FIG. 5 comprises a schematic view as configured in accordance with various embodiments of these teachings.

And FIG. 5 schematically depicts a double half-fan solution employing two gantry paths and in particular depicts the use of half-fan arcs corresponding to radiation cones where a first pair of illustrative opposing radiation cones that correspond to a first gantry path 304 that combine to fully irradiate the target structure that constitutes the treatment volume 105 for this patient 104 are denoted by reference numerals 302 and 303. A second pair of illustrative opposing radiation cones that correspond to a second gantry path 503 (where the radiation source 115 is moving backwards along the gantry path that it previously moved forward on) that combine to again fully irradiate the target structure that constitutes the treatment volume 105 are denoted by reference numerals 501 and 502.

Those skilled in the art will recognize that a wide variety of modifications, alterations, and combinations can be made with respect to the above described embodiments without departing from the scope of the invention. As one example in these regards, these teachings will accommodate using an automatic tool to convert a user-defined, normal, isocentric arc into the requisite half-fan arc. As another example, these teachings will accommodate allowing a user to request a desired width of an overlap region between corresponding half arcs. And as yet another example in these regards, these teachings will accommodate including conversion of the solution to include use of half-fan arcs as part of a collimator angle optimization process. Accordingly, such modifications, alterations, and combinations are to be viewed as being within the ambit of the inventive concept.

What is claimed is:

1. A method to radiate a treatment target in a patient during a radiation treatment session with a radiation treatment platform having a moving source of radiation using an optimized radiation treatment plan, the method comprising:
configuring the radiation treatment platform in a half-fan trajectory arrangement;
beginning the radiation treatment session with the source of radiation in a first location and an isocenter for the treatment target in a first position within the treatment target;
during the radiation treatment session, moving the source of radiation from the first location in synchronization with moving the isocenter from the first position to a second position within the treatment target.

2. The method of claim 1 wherein moving the isocenter comprises moving a patient-supporting couch that comprises a part of the radiation treatment platform.

3. The method of claim 2 wherein moving the source of radiation comprises moving the source of radiation via a gantry that comprises a part of the radiation treatment platform.

4. The method of claim 1 wherein moving the source of radiation comprises moving the source of radiation along an arcuate pathway.

5. The method of claim 4 wherein the arcuate pathway comprises an arc exceeding 180 degrees in curvature about the patient.

6. The method of claim 5 wherein the arcuate pathway comprises an arc of at least 350 degrees in curvature about the patient.

7. The method of claim 1 further comprising:
specifying the half-fan trajectory arrangement for the radiation treatment platform;
optimizing a radiation treatment plan for radiation treatment platform parameters other than the half-fan trajectory arrangement to provide the optimized radiation treatment plan.

8. The method of claim 7 wherein specifying the half-fan trajectory arrangement comprises specifying a pre-determined trajectory pattern.

9. The method of claim 8 wherein optimizing a radiation treatment plan for radiation treatment platform parameters other than the half-fan trajectory arrangement comprises not optimizing the pre-determined trajectory pattern.

10. The method of claim 1 wherein moving the source of radiation from the first location in synchronization with moving the isocenter from the first position comprises simultaneously moving, for at least part of the radiation treatment session, both the source of radiation and the isocenter.

11. An apparatus to radiate a treatment target in a patient during a radiation treatment session, the apparatus comprising:
a radiation treatment platform having a moving source of radiation and configured in a half-fan trajectory arrangement;

a control circuit configured to administer radiation to the treatment target per an optimized radiation treatment plan by:

beginning the radiation treatment session with the source of radiation in a first location and an isocenter for the treatment target in a first position within the treatment target; and during the radiation treatment session, moving the source of radiation from the first location in synchronization with moving the isocenter from the first position to a second position within the treatment target.

12. The apparatus of claim 11 wherein the radiation treatment platform includes a patient-supporting couch and wherein the control circuit is configured to move the isocenter by moving the patient-supporting couch.

13. The apparatus of claim 12 wherein the control circuit is configured to move the source of radiation by moving the source of radiation via a gantry that comprises a part of the radiation treatment platform.

14. The apparatus of claim 11 wherein the radiation treatment platform is configured to move the source of radiation along an arcuate pathway.

15. The apparatus of claim 14 wherein the arcuate pathway comprises an arc exceeding 180 degrees in curvature about the patient.

16. The apparatus of claim 15 wherein the arcuate pathway comprises an arc of at least 350 degrees in curvature about the patient.

17. The apparatus of claim 11 wherein the control circuit is further configured to:

specify the half-fan trajectory arrangement for the radiation treatment platform;

optimize a radiation treatment plan for the radiation treatment platform for radiation treatment platform parameters other than the half-fan trajectory arrangement to provide the optimized radiation treatment plan.

18. The apparatus of claim 17 wherein specifying the half-fan trajectory arrangement comprises specifying a pre-determined trajectory pattern.

19. The apparatus of claim 18 wherein the control circuit is configured to optimize a radiation treatment plan for radiation treatment platform parameters other than the half-fan trajectory arrangement by not optimizing the pre-determined trajectory pattern.

20. The apparatus of claim 11 wherein the control circuit is configured to move the source of radiation from the first location in synchronization with moving the isocenter from the first position by simultaneously moving, for at least part of the radiation treatment session, both the source of radiation and the isocenter.

* * * * *